United States Patent [19]

Prisbylla

[11] Patent Number: 4,481,026
[45] Date of Patent: Nov. 6, 1984

[54] ALUMINUM N-PHOSPHONOMETHYLGLYCINE AND ITS USE AS A HERBICIDE

[75] Inventor: Michael P. Prisbylla, Richmond, Calif.

[73] Assignee: Stauffer Chemical Co., Westport, Conn.

[21] Appl. No.: 541,504

[22] Filed: Oct. 17, 1983

Related U.S. Application Data

[63] Continuation-in-part of Ser. No. 442,067, Nov. 16, 1982, abandoned.

[51] Int. Cl.³ .......................... E05B 65/46; C07F 5/06
[52] U.S. Cl. ..................................... 71/86; 260/448 R
[58] Field of Search ........................ 260/448 R, 502.5; 71/86

[56] References Cited

U.S. PATENT DOCUMENTS

| | | | |
|---|---|---|---|
| 3,442,922 | 5/1969 | Langer | 260/448 R X |
| 3,455,675 | 7/1969 | Irani | 71/86 |
| 3,850,608 | 11/1974 | Hamm | 71/86 X |
| 3,929,450 | 12/1975 | Hamm et al. | 71/86 |
| 4,148,624 | 4/1979 | Maier | 260/502.5 F X |
| 4,202,706 | 5/1980 | Newell et al. | 260/502.5 R X |
| 4,341,549 | 7/1982 | Large et al. | 260/502.5 F X |
| 4,384,880 | 5/1983 | Large | 260/502.5 F X |

Primary Examiner—Helen M. S. Sneed
Attorney, Agent, or Firm—Harry A. Pacini

[57] ABSTRACT

The aluminum salt of N-phosphonomethylglycine as a unique compound which has utility as a post-emergence herbicide and is also useful as a plant growth regulator; and herbicidal and growth regulating compositions comprising the compound aluminum N-phosphonomethylglycine.

11 Claims, No Drawings

ALUMINUM N-PHOSPHONOMETHYLGLYCINE AND ITS USE AS A HERBICIDE

CROSS REFERENCE TO RELATED APPLICATION

This application is a continuation-in-part application of Ser. No. 442,067, filed Nov. 16, 1982 now abandoned.

BACKGROUND OF THE INVENTION

This invention is directed to a novel chemical compound and its use in controlling weeds and regulating the natural growth or development of plants.

It is known that various features of plant growth can be modified or regulated to produce a variety of beneficial effects. For instance, plants can be defoliated and leaf growth inhibited while the productive plant parts remain unaffected. Such action often stimulates extra growth on the productive plant parts and facilitates harvesting operations. Chemical agents producing these effects are particularly useful in flax, cotton, and bean crops, and other crops of a similar nature. While defoliation results in the killing of leaves, it is not a herbicidal action since it does not harm the remainder of the plant. Indeed, killing of the treated plant is undesirable when defoliation is sought, since leaves will continue to adhere to a dead plant.

Another response demonstrated by plant growth regulants is the general retardation of vegetative growth. This response has a wide variety of beneficial features. In certain plants it causes a diminution or elimination of the normal apical dominance, leading to a shorter main stem and increased lateral branching. Smaller, bushier plants with increased resistance to drought and pest infestation are the result. Retardation of vegetative growth is also useful in turf grasses for lessening the vertical growth rate, enhancing root development, and producing a denser, sturdier turf. The retardation of turf grasses also serves to increase the interval between mowings of lawns, golf courses and similar grassy areas.

PRIOR ART

Hensley et al., *Weed Research*, 1978, vol. 18, pp. 287-291 describes the effect of various cations on the activity of N-phosphonomethylglycine. The presence of aluminum in clays and organic matter appeared to inactivate or significantly reduce the activity of N-phosphonomethylglycine with respect to the inhibitory effect of the N-phosphonomethylglycine on root growth. Therefore, toxicity inactivation by the presence of aluminum is taught by this reference. Root bioassays to determine the degree of adsorption of N-phosphonomethylglycine by the different cations on a hybrid variety of sorghum was used in the test procedures. It is postulated that the aluminum could be chelated by the N-phosphonomethylglycine thereby causing the inactivation of the N-phosphonomethylglycine. This is contrary to the teachings and findings of the present invention.

Hanson et al. (1976) (Abstract) *Proc. 26th South. Weed Sci. Soc.*, 49, teaches adsorption to mineral colloids and organic material through the formation of aluminum complexes with N-phosphonomethylglycine. Sprankel et al. (1975) *Weed Science*, 23, pp. 229-234 found that N-phosphonomethylglycine was rapidly inactivated by organic and mineral soils and that aluminum-containing saturated clays and organic matter had absorbed more N-phosphonomethylglycine than unsaturated or non-aluminum-containing materials. Sprenkel et al. postulated that the N-phosphonomethylglycine may be binding to the soil containing aluminum, thereby causing the inactivation.

Additional references have shown reduced N-phosphonomethylglycine phytototoxicity due to the presence of aluminum: Wills, G. D., (1973) *Abstr. Weed. Sci. Soc. Am.*, p. 59; and Phillips, (1975), *Proc. North Cent. Weed Control Conf.*, 30, p. 115.

BRIEF DESCRIPTION OF THE INVENTION

It has now been discovered that aluminum N-phosphonomethylglycine is a unique and novel compound which possesses agricultural utility, for example, useful in regulating the natural growth or development to plants and to be phytotoxic to plants when used in an herbicidally effective amount. Accordingly, the invention relates to a method of controlling undesirable vegetation, comprising applying to the vegetation in postemergent state a herbicidally effective amount of the compound. Herbidical effects are generally achieved with a higher application rate than plant growth regulant effects. The compound is particularly effective in controlling grass weeds. The term "herbicidally effective amount" designates any amount which will kill a plant or any portion thereof. The term "plants" is intended to include germinant seeds, emerging seedlings, and established vegetation, including both roots and above-ground portions. In addition, aluminum N-phosphonomethylglycine has been found to possess these distinct and desirable properties not suggested by the prior art.

DETAILED DESCRIPTION OF THE INVENTION

Herbicidal effects are achieved by adversely affecting natural growth or development of plants, and the strength of the application can be varied to achieve the desired result. The compound of the instant invention serves to regulate the natural growth or development of treated plants in a number of diverse ways, and it should be understood that the regulatory effects will vary from one plant species to the next or from one application rate to the next.

The compound of this invention is readily prepared from N-phosphonomethylglycine by reacting the latter with an aluminum source in the presence of water to form an aqueous solution. The combination within the solution is heated for a predetermined time at reflux temperature and then allowed to cool, filtered and the aqueous solution is concentrated to give the final result. When using this procedure for forming the compound of this invention, it has been found that the mole ratio of aluminum cation to N-phosphonomethylglycine anion is 1 to 4.

Alternatively, the compound of this invention can be made by reacting an aluminum salt, such as aluminum isopropoxide, with an aqueous solution of N-phosphonomethylglycine. After heating to reflux for a predetermined time, the product can be isolated from the aqueous solution in the usual manner of cooling, filtering and concentrating the resulting solution. As should be apparent, the source of aluminum can be chosen from a wide range of aluminum compounds, both organic and inorganic.

The aluminum source can be in any form, such as aluminum oxides or aluminum hydroxides which are commercially available. N-Phosphonomethylglycine is a commercially available material that can be prepared by the phosphonomethylation of glycine, by reaction of ethyl glycinate with formaldehyde and diethylphosphite, or the oxidation of the N-phosphinomethylglycine. Such methods are described in U.S. Pat. No. 3,799,758 (Franz, Mar. 26, 1974).

Examples 1 and 2 illustrate the preparation of the aluminum compound and Examples 3 and 4 illustrate the nonselective herbicidal activity and plant growth activity, respectively. These examples are merely illustrative, non-limiting demonstrations of the preparation of the compound of the present invention and of its effectiveness in controlling undesirable vegetation.

EXAMPLE 1

Preparation of Aluminum N-Phosphonomethylglycine

Aluminum hydroxide (1.17 grams, 0.015 mole) was combined with 7.5 grams (g) (0.045 mole) of N-phosphonomethylglycine in a 200 milliliters (ml) flask containing 60 ml of deionized water. The flask was equipped with a magnetic stirrer. This solution was heated at reflux temperature for one hour and then let stand overnight at room temperature. The reaction mixture the next day contained more solid material after cooling overnight. The solution was again heated at reflux for 3 more hours, and then cooled to room temperature. The material was then filtered to remove the solids and the aqueous filtrate was stripped at 30° C. and 1 mm of mercury. The residue was 8.0 g of a white powder which was water-soluble, having a melting point of 231° C. The white powder was subjected to standard analytical procedures and the subject compound was confirmed as one part aluminum and four parts of the N-phosphonomethylglycine anion.

EXAMPLE 2

Aluminum isopropoxide (1.02 g, 0.005 mole) and N-phosphonomethylglycine (0.02 mole, 3.338 g) were suspended in 150 ml water and then briefly heated to reflux which solubilized the reactants. The solution was cooled to give a clear solution which was then filtered and concentrated to obtain 3.66 g (quantative yield) of a white powder. The compound is water-soluble. Analysis: theoretical—carbon 18.65%, hydrogen 4.79%, nitrogen 7.25%, phosphorus 16.06%, aluminum 3.49%; actual—carbon 18.79%, hydrogen 4.59%, nitrogen 7.39%, phosphorus 16.34%, aluminum 3.50%.

This analysis corresponds to a ratio of one part aluminum per four parts of N-phosphonomethylglycine as a tetrahydrate.

By using transmission electron microscopy with electron diffraction on tiny crystallites an electron diffraction pattern was obtained for the compound of this invention. Three phases were observed with different triclinic unit cells. The unit cell parameters are given in the following table.

|   | 1 | 2 | 3 |
|---|---|---|---|
| A | 27.53Å | 22.91Å | 20.32Å |
| B | 19.50Å | 16.22Å | 14.39Å |
| C | 18.61Å | 18.46Å | 18.51Å |
| α | 72° | 72° | 72° |
| β | 60° | 60° | 60° |
| ∂ | 40° | 50° | 60° |

All lines of the X-ray diffraction pattern (56) were accounted for with these 3-unit cells. The range of reflections for the aluminum compound is 2.57–14.2 Å whereas the range of reflections for N-phosphonomethylglycine is 1.37–8.37 Å.

Nuclear magnetic resonance of an aqueous solution showed a very complex dynamic equilibrium exists in this environment. In the solid form the aluminum compound can exist in more than one species of configuration, therefore it is difficult to designate one specific structure for the aluminum compound.

EXAMPLE 3

Herbicidal Activity

This example demonstrates the postemergence herbicidal activity of the subject compound.

Aluminum planting flats measuring $15.2 \times 22.9 \times 8.9$ cm were filled to a depth of 7.6 cm with loamy sand soil, containing 50 parts per million (ppm) each of the commercial fungicide cis-N[(trichloromethyl)thio]-4-cyclohexene-1,2-dicarboximide (Captan) and 17-17-17 fertilizer (percentages of $N-P_2O_5-K_2O$ on a weight basis). Several rows were impressed across the width of each flat and a variety of seeds of both grass and broadleaf plant species were planted. The weed species used are listed below:

| Grasses: | | Broadleaf Weeds: | |
|---|---|---|---|
| DB | downybrome | AMG | annual morning glory |
| ARG | annual ryegrass | CB | cocklebur |
| WG | watergrass | SES | sesbania |
| SHC | shattercane | VL | velvetleaf |
| WO | wild oats | MD | mustard |
| FT | foxtail | SP | sicklepod |
| | | PW | pigweed |
| Crops: | | Other | |
| SOY | soybeans | YNG | yellow nutsedge |
| RE | rice | | |
| COT | cotton | | |
| CN | corn | | |
| WH | wheat | | |
| ML | milo | | |
| SB | sugar beets | | |

The broad leaf species were seeded first, and the grasses were seeded four days later. Ample seeds of each species were planted to produce 4 to 50 seedlings per row after emergence, depending on the size of each plant.

Ten days after the grasses were seeded, the emerged seedlings of all species were sprayed with aqueous solutions of the test compounds. The solutions were prepared to such dilutions that a spray rate of 80 gallons per acre (750 liters per hectare) gave from 0.25 to 2.0 pounds of test compound per acre (0.28 to 2.24 kilograms per hectare) as desired for each test. Additional flats not treated at all were used as standards for measuring the extent of weed control in the treated flats.

Nineteen days later, the test flats were compared to the standards and the weeds in each row were rated visually in terms of percent control ranging from 0% to 100%, with 0% representing the same degree of growth as the same row in the standard and 100% representing complete kill of all weeds in the row. All types of plant injury were taken into consideration. The results are shown in Table I.

TABLE I

HERBICIDE TEST RESULTS

TEST COMPOUND: Aluminum N—Phosphonomethylglycine

| Application Rate (lb/A) | GRASSES | | | | | | | Other |
|---|---|---|---|---|---|---|---|---|
| | DB | FT | ARG | WG | SHC | WO | AVE* | YNG |
| 1/4 | 50 | 100 | 30 | 70 | 70 | 30 | 58 | 0 |
| 1/2 | 60 | 100 | 40 | 90 | 80 | 65 | 73 | 45 |
| 1 | 70 | 100 | 55 | 100 | 100 | 80 | 84 | 70 |
| 2 | 80 | 100 | 80 | 100 | 100 | 95 | 93 | 75 |

| | BROADLEAF WEEDS | | | | | | | |
|---|---|---|---|---|---|---|---|---|
| | AMG | CB | SES | VL | MD | SP | PW | AVE |
| 1/4 | 60 | 40 | 40 | 50 | 75 | 50 | 40 | 51 |
| 1/2 | 65 | 50 | 70 | 70 | 80 | 60 | 50 | 64 |
| 1 | 70 | 70 | 75 | 75 | 90 | 65 | 60 | 72 |
| 2 | 75 | 85 | 80 | 80 | 100 | 70 | 70 | 80 |

| | CROPS | | | | | | |
|---|---|---|---|---|---|---|---|
| | SOY | RC | COT | CN | WH | ML | SB |
| 1/4 | 45 | 0 | 50 | 70 | 60 | 40 | 45 |
| 1/2 | 55 | 40 | 60 | 90 | 75 | 75 | 70 |
| 1 | 60 | 50 | 70 | 100 | 100 | 90 | 75 |
| 2 | 75 | 95 | 80 | 100 | 100 | 100 | 85 |

*AVE: average

EXAMPLE 4

This example illustrates the utility of the compound of this invention in regulating the growth of sweet sorghum (Sorghum vulgare).

The following test procedure was used:

A series of fiber pots (5 inches×5 inches×5 inches) were each filled with sandy loam soil containing 150 ppm of 17-17-17 fertilizer (i.e., comprising 17% by weight each of N, $P_2O_5$, and $K_2O$). Sorghum seeds were seeded in each pot in a single row and the pots were placed in a greenhouse in which the temperature was maintained at 27° C. during the day and 21° C. at night. During the next five weeks, the emerging plants were thinned down to two per pot. The pots were fertilized periodically with 17-17-17 fertilizer.

The plants were sprayed approximately eight weeks after seeding with a solution consisting of the test compound dissolved in equal portions (1:1) of acetone and water containing 0.5% Tween 20 ® (polyoxyethylene sorbitan monolaurate). The spraying system was a linear spray table. The test solution was sprayed at a rate of 80 gallons per acre (750 liters per hectare). The concentration of the solution was predetermined to produce the desired application rate in pound per acre (lb/A) when sprayed to the plants at a total volume of 80 gallons per acre. The concentration was selected to correspond to an application rate of 0.0625, 0.125 and 0.25 lb/A (0.074, 0.15 and 0.287 kilograms per hectare).

Following treatment, the plants were placed in the greenhouse for an additional 14 days. Sugar content was determined five days later after cutting the stalks at soil level. The stalks were squeezed to obtain a few drops of liquid of plant fluid. Total dissolved solids percent of the fluid (TDS %) was measured with a hand-held refractor, and is expressed as weight percent of the juice.

Two replications were performed at each application rate. In addition, untreated plants were included as check plants for comparison. The results are shown in Tables II and III.

Table II lists the data pertaining to symptoms and percent total dissolved solid. The data listed are averages of each replication. Table III lists averages of the measurements taken on the treatment means for the total dissolved solids at each rate of treatment. The data indicate an increase in total dissolved solids as compared to the check plant averages.

TABLE II

Total Dissolved Solids of Immature Plants
Average of 2 Replications Each

| Application Rate (lb/A) | Rep. | Rating | Symptoms[a] | TDS % |
|---|---|---|---|---|
| 1/4 | 1 | 2 | St, Ch | 5.8 |
| | 2 | 3 | S̄t, Ch | 7.1 |
| 1/8 | 1 | 1 | S̄t, Ch | 6.0 |
| | 2 | 1 | S̄t, Ch | 5.3 |
| 1/16 | 1 | 0 | — | 4.2 |
| | 2 | 0 | | 4.5 |
| 0 | 1 | 0 | | 4.5 |
| | 2 | 0 | | 5.3 |

TABLE III

Table of Treatment Means

| Application Rate (lb/A) | TDS % | Percent Increase in TDS % |
|---|---|---|
| 1/4 | 6.5 | 33 |
| 1/8 | 5.7 | 16 |
| 1/16 | 4.5 | −8 |
| 0 | 4.9 | 0 |

St = stunting (shortned internodes)
Ch = chlorosis
Line under symptoms means that is the main symptom.

METHODS OF APPLICATION

Whether it is used as a plant growth regulator or as a herbicide, the compound of the present invention is most useful when applied directly to the plants after their emergence from the soil. For application at a field site, the compound is generally embodied in an agriculturally suitable formation containing additional ingredients and diluent carriers to aid in its dispersal. Examples of such ingredients or carriers are water, organic solvents, dusts, granules, surface active agents, water-in-oil and oil-in-water emulsions, wetting agents, dispersing agents, and emulsifiers. The formulation generally takes the form of a dust, solution, emulsifiable concentrate, or wettable powder.

A. DUSTS

Dusts are dense powder compositions which combine the active compounds with a dense, free-flowing solid carrier. They are intended for application in dry form and are designed to settle rapidly to avoid being wind-borne to areas where their presence is not desired.

The carrier may be of mineral or vegetable origin, and is preferably an organic or inorganic powder of high bulk density, low surface area, and low liquid absorptivity. Suitable carriers include micaceous talcs, pyrophyllite, dense kaolin clays, tobacco dust, and ground calcium phosphate rock.

The performance of a dust is sometimes aided by the inclusion of a liquid or solid wetting agent, of ionic, anionic, or nonionic character. Preferred wetting agents include alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Dispersants are also useful in the same dust compositions. Typical dispersants include methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N-(long chain acid) taurates.

In addition, inert absorptive grinding aids are frequently included in dust compositions to aid in the manufacturing of the dust. Suitable grinding aids include attapulgite clay, diatomaceous silica, synthetic fine silica and synthetic calcium and magnesium silicates.

In typical dust compositions, carriers are usually present in concentrations of from about 30 to 90 weight percent of the total composition. The grinding aid usually constitutes about 5 to 50 weight percent, and the wetting agent up to about 1.0 weight percent. Dispersants, when present, constitute up to about 0.5 weight percent, and minor amounts of anticaking and antistatic agents may also be present. The particle size of the entire composition is usually about 30 to 50 microns.

B. SOLUTIONS

Aqueous solutions of the active compounds are prepared such that application at the rate of about 1 to about 200 gallons of solution per acre (about 9 to about 1875 liters per hectare) will provide the required amount of active ingredient. A small amount of non-phytotoxic surfactant typically between 0.05% and 0.5% by weight is usually included to improve the wetting ability of the solution and thus its distribution over the plant surface. Anionic, cationic, nonionic, ampholytic, and zwitterionic surfactants are all useful in this regard. From the standpoint of ecomony and convenience, liquid compositions using water as a diluent are preferred.

Suitable anionic surfactants include alkali metal, ammonium, and amine salts of fatty alcohol sulfates having from 8–18 carbon atoms in the fatty chain and sodium salts of alkyl benzene sulfonates having from 9 to 15 carbon atoms in the alkyl chain. Suitable cationic surfactants include dimethyl dialkyl quaternary ammonium halides with alkyl chains of 8 to 18 carbon atoms. Suitable nonionic surfactants include polyoxyethylene adducts of fatty alcohols having 10 to 18 carbon atoms, polyethylene oxide condensates of alkyl phenols with alkyl chains of 6 to 12 carbon atoms and 5 to 25 moles of ethylene oxide condensed onto each mole of alkyl phenol, and polyethylene oxide condensates of sorbitan esters with 10 to 40 moles of ethylene oxide condensed onto each mole of sobitan ester. Suitable ampholytic surfactants include secondary and tertiary aliphatic amine derivatives with one aliphatic substituent containing 8 to 18 carbon atoms and another containing an anionic watersolubilizng group such as a sulfate or sulfonate. Sodium-3-dodecylaminopropionate and sodium-3-dodecyl amino propane sulfonate are examples. Suitable zwitterionic surfactants include derivatives of aliphatic quaternary ammonium compounds with one aliphatic substituent containing 8 to 18 carbon atoms and another containing an anionic water-solubilizing group. Examples of are 3-(N,N-dimethyl-N-hexadecylammonio)propane-1-sulfate and 3-(N,N-dimethyl-N-hexadecylammonio)-2-hydroxy propane-1-sulfonate.

C. EMULSIFIABLE CONCENTRATES

Emulsifiable concentrates are solutions in which the active materials and an emulsifying agent are dissolved in a non-watermiscible solvent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil-soluble petroleum sulfonates, or preferably mixtures of these emulsifying agents. Such emulsifying agents usually comprise about 1 to 10 weight percent of the total composition.

Typical emulsifiable concentrates contain about 15 to 50 weight percent active material, about 40 to 82 weight percent solvent, and about 1 to 10 weight percent emulsifier. Other additives such as spreading agents and stickers can also be included.

D. WETTABLE POWDERS

Wettable powders are water-dispersible compositions containing the active material, an inert solid extender, and one or more surfactants to provide rapid wetting and prevent floccuation when suspended in water.

Suitable solid extenders include both natural minerals and materials derived synthetically from such minerals. Examples include kaolinites, attapulgite clay, montmorillonite clays, synthetic silicas, synthetic magnesium silicate and calcium sulfate dihydrate.

Suitable surfactants include both nonionic and anionic types, and function as wetting agents and dispersants. Usually one of each is included. Preferred wetting agents are alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N(long chain acid) taurates.

Typical wettable powders contain 25 to 90 percent active material, 0.5 to 2.0 percent wetting agent, 0.25 to 5.0 percent dispersant, and from 9.25 to 74.25 weight percent inert extender. Frequently, 0.1 to 1.0 percent of the extender is replaced by a corrosion inhibitor and/or an antifoaming agent.

E. IN GENERAL

In general, any conventional agriculturally useful composition for use in postemergence method of application can be used, including common dusting or spraying equipment. The amount of active ingredient which is effective in producing the desired result, be it herbidical or growth-regulating, depends on the nature of the plant species to be controlled and the prevailing conditions. Herbidical effects are usually achieved at 0.1 to 50 pounds active ingredient per acre, preferably 1 to 10, while plant growth regulation is usually achieved at 0.1 to 20 pounds active ingredient per acre, preferably 0.5 to 5.

What is claimed is:

1. The compound aluminum N-phosphonomethylglycine.

2. The compound of claim 1 wherein the molar ratio of aluminum to acid anion is substantially 1 to 4.

3. The compound of claim 1 which is substantially in a hydrated form.

4. A herbicidal composition comprising a herbidically effective amount of the compound of claim 1 admixed with at least one inert adjuvant carrier.

5. The method of controlling undesired vegetation comprising adding to the habitat where control is desired a herbicidally effective amount of the compound of claim 1.

6. The method of controlling undesired vegetation comprising adding to the habitat where control is desired a herbicidally effective amount of the composition of claim 4.

7. A composition for use as a herbicide comprising a herbicidally effective amount of an aluminum compound of N-phosphonomethylglycine wherein the molar ratio of aluminum to acid is substantially 1 to 4 and at least one adjuvant.

8. An aluminum N-phosphonomethylglycine compound prepared by the steps of reacting N-phosphonomethylglycine and an aluminum compound in the presence of water, heating to reflux, cooling, filtering and concentrating the filtrate.

9. The compound of claim 8 wherein the aluminum compound is aluminum hydroxide.

10. The compound of claim 8 wherein the aluminum compound is aluminum isopropoxide.

11. A composition for use as a plant growth regulator comprising a herbicidally effective amount of an aluminum compound of N-phosphonomethylglycine wherein the molar ratio of aluminum to acid is substantially 1 to 4 and at least one adjuvant.

* * * * *

UNITED STATES PATENT AND TRADEMARK OFFICE
CERTIFICATE OF CORRECTION

PATENT NO. : 4,481,026

DATED : November 6, 1984

INVENTOR(S) : Michael P. Prisbylla

It is certified that error appears in the above-identified patent and that said Letters Patent is hereby corrected as shown below:

In Column 6, line 40, "formation" should read "formulation"....

In Column 7, line 50, "sobitan" should read "sorbitan"...

In column 7, line 62, "propane-1-sulfate" should read "propane-1-sulfonate"

Signed and Sealed this

Sixth Day of August 1985

[SEAL]

Attest:

DONALD J. QUIGG

Attesting Officer — Acting Commissioner of Patents and Trademarks